US00PP35552P2

(12) United States Plant Patent
Clark

(10) Patent No.: US PP35,552 P2
(45) Date of Patent: Dec. 19, 2023

(54) BLACKBERRY PLANT NAMED 'APF-409T'

(50) Latin Name: ***Rubus* subgenus *Rubus* Watson**
Varietal Denomination: APF-409T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: The Board of Trustees of The University of Arkansas, Little Rock, AR (US)

( * ) Notice: Subject to any disclaimer, the term of this patent is extended or adjusted under 35 U.S.C. 154(b) by 0 days.

(21) Appl. No.: 18/445,118

(22) Filed: Apr. 14, 2023

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499; A01H 5/08
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark |
| PP11,865 | P2 | 5/2001 | Clark |
| PP14,935 | P2 | 6/2004 | Clark |
| PP15,788 | P2 | 6/2005 | Clark |
| PP16,989 | P3 | 8/2006 | Clark |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz |
| PP26,405 | P3 | 2/2016 | Clark |
| PP26,413 | P3 | 2/2016 | Ortiz |
| PP26,990 | P3 | 8/2016 | Clark |
| PP27,032 | P2 | 8/2016 | Clark |
| PP27,401 | P3 | 11/2016 | Clark |
| PP28,598 | P3 | 11/2017 | Clark |
| PP34,867 | P2 | 12/2022 | Clark |

OTHER PUBLICATIONS

Clark, J.R. et al., "'APF-45' primocane-fruiting blackberry," (2011) Hort. Science 46(4):670-673.
Ruple, A. et al., "An evaluation of fertility in Arkansas primocane-fruiting blackberries," (2010) Hort. Science 45:1-6.
Daugovish, O., et al. "Blackberry and Raspberry Cultivar Evaluations in Coastal California." HortTechnology 31.4 (2021): 552-558.
Plant U.S. Appl. No. 17/968,508, filed Oct. 18, 2022, Blackberry Plant Named 'APF-404T', John R. Clark inventor, The Board of Trustees of the University of Arkansas.

*Primary Examiner* — Keith O. Robinson
(74) *Attorney, Agent, or Firm* — Quarles & Brady LLP

(57) ABSTRACT

Description and specifications of a new and distinct cultivar of blackberry plant named 'APF-409T' which originated from seed produced by a hand-pollinated cross of Arkansas selections 'A-2504T' (an unpatented breeding selection) x 'APF-295T' (an unpatented breeding selection) is provided. This new cultivar of blackberry plant can be distinguished by its excellent plant health, thornless canes, strong primocane-fruiting tendency, and early season of fruit ripening on both floricanes and primocanes.

4 Drawing Sheets

Latin name: *Rubus* subgenus *Rubus* Watson.
Varietal denomination: 'APF-409T'.

BACKGROUND

The new primocane-fruiting blackberry plant called 'APF-409T' is described herein. The new plant originated from a hand-pollinated cross of Arkansas selections 'A-2504T' (an unpatented breeding selection) x 'APF-295T' (an unpatented breeding selection) made in 2012. The seeds resulting from this controlled hybridization were germinated in a greenhouse in the spring of 2013 and planted in a field near Clarksville, Ark. (West-Central Arkansas). The seedlings fruited in the summer of 2014 and one seedling, designated 'APF-409T' was selected. It was selected for excellent plant health, thornless canes, strong primocane-fruiting tendency, and early season of fruit ripening on both floricanes and primocanes.

SUMMARY OF THE INVENTION

The new and distinct cultivar of blackberry originated from a hand-pollinated cross of Arkansas selections 'A-2504T' (an unpatented breeding selection) x 'APF-295T' (an unpatented breeding selection) made in 2012. The botanical designation of the new cultivar of blackberry is *Rubus* L. subgenus *Rubus* Watson.

The seeds resulting from this controlled hybridization were germinated in a greenhouse in the winter to early spring of 2012-2013 and planted in a field near Clarksville, Ark. The seedlings fruited on floricanes in the summer of 2014 and one seedling, designated 'APF-409T', was selected for its excellent plant health, thornless canes, strong primocane-fruiting tendency, and early season of fruit ripening on both floricanes and primocanes.

During winter 2014-2015, the original plant selection was propagated asexually from root cuttings at the above-noted location, and a test row of 10 plants was established.

The new cultivar has been asexually multiplied since 2014 by the use of rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants shown in the figures were three years of age.

DETAILED DESCRIPTION OF THE NEW CULTIVAR 'APF-409T'

Figure 1:
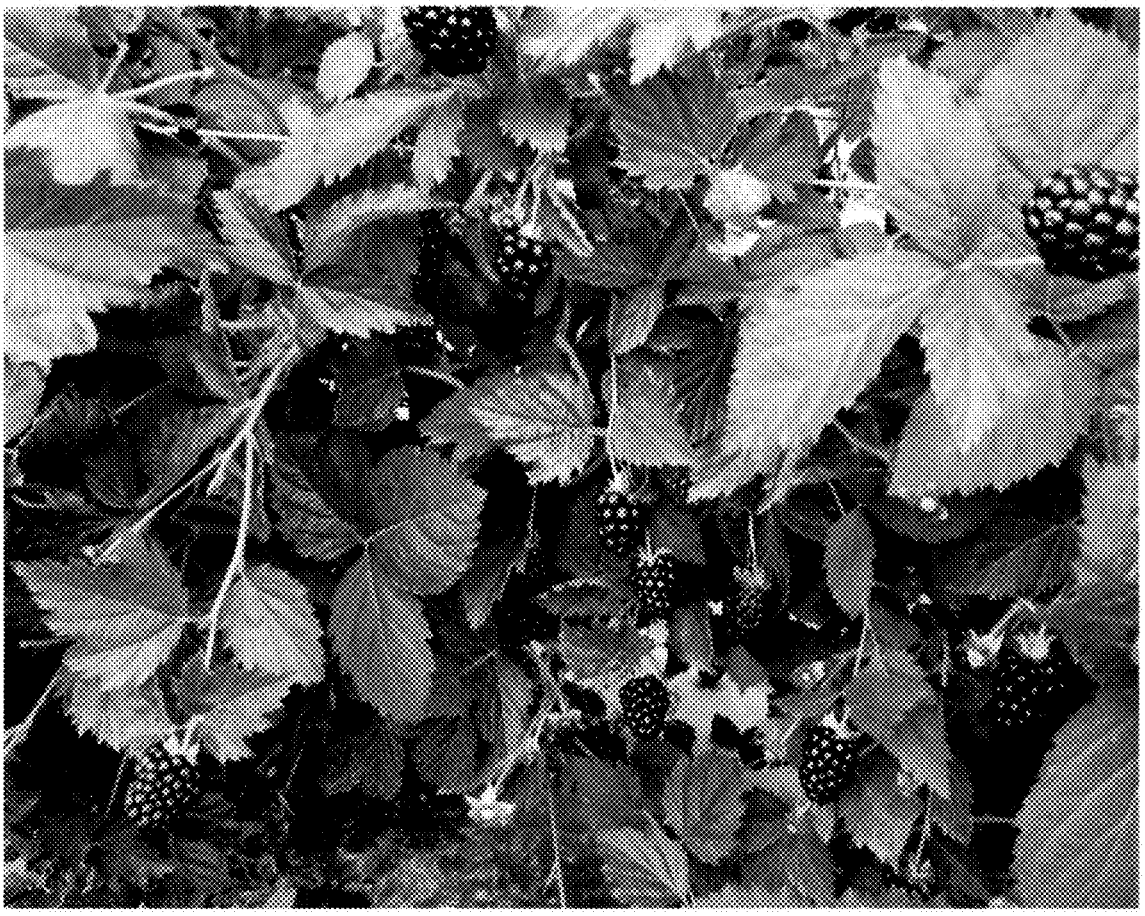
FIG. 1 is a photograph of fruit of 'APF-409T' borne on a floricane of a three-year-old plant near Clarksville, Ark.
Figure 2:
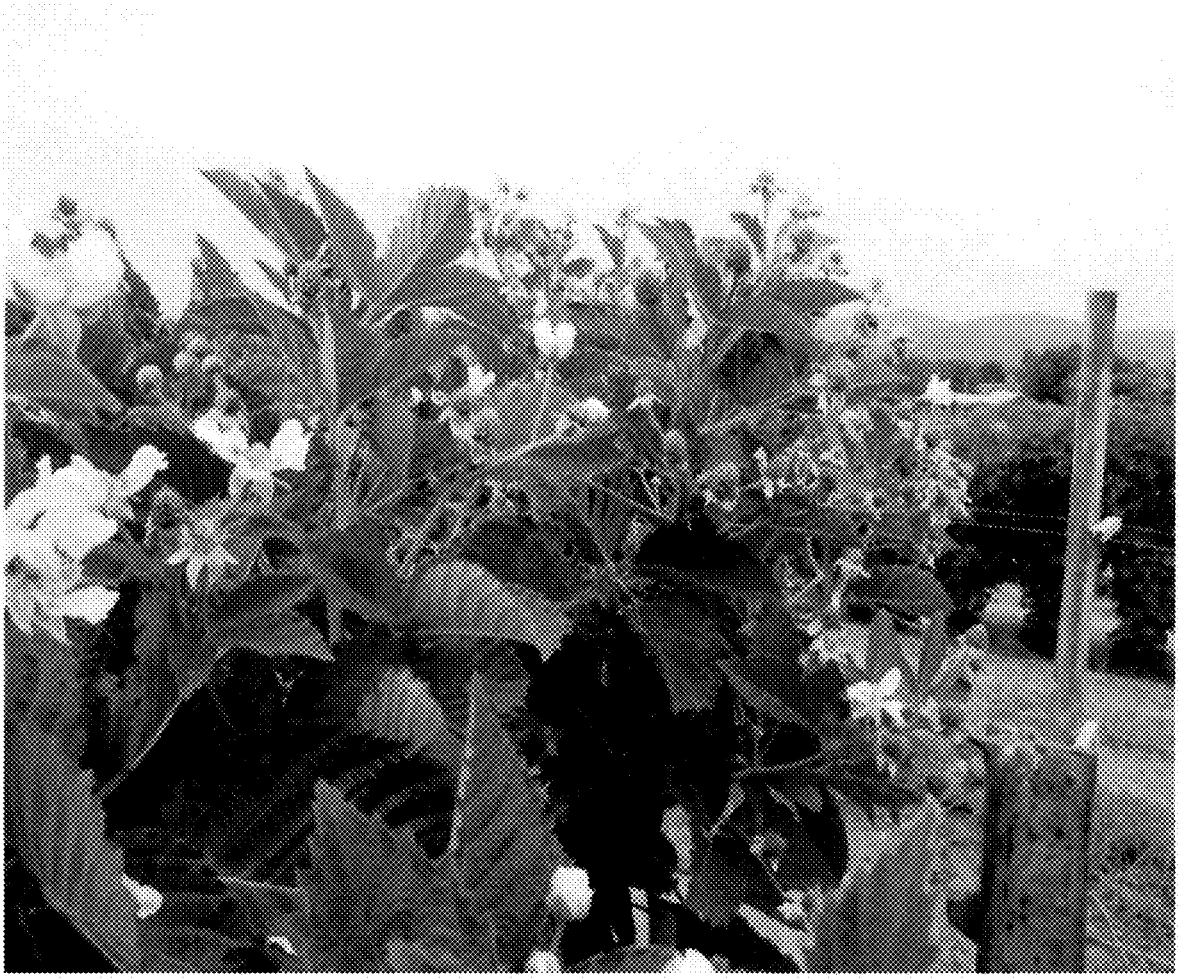
FIG. 2 is a photograph of primocane flower buds, flowers, and immature fruit on a three-year-old plant of 'APF-409T' near Clarksville, Ark.
Figure 3:
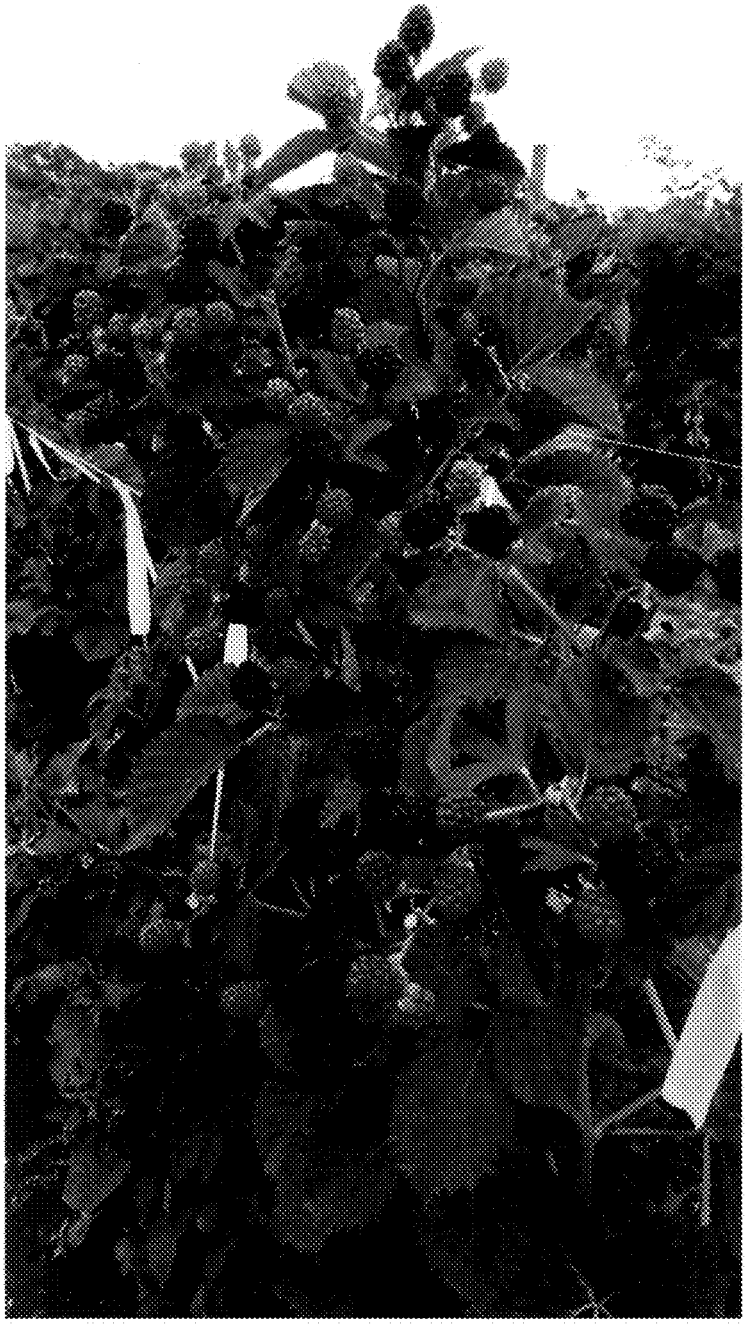
FIG. 3 is a photograph of primocane fruit on a three-year-old plant of 'APF-409T', near Clarksville, Ark.
Figure 4:
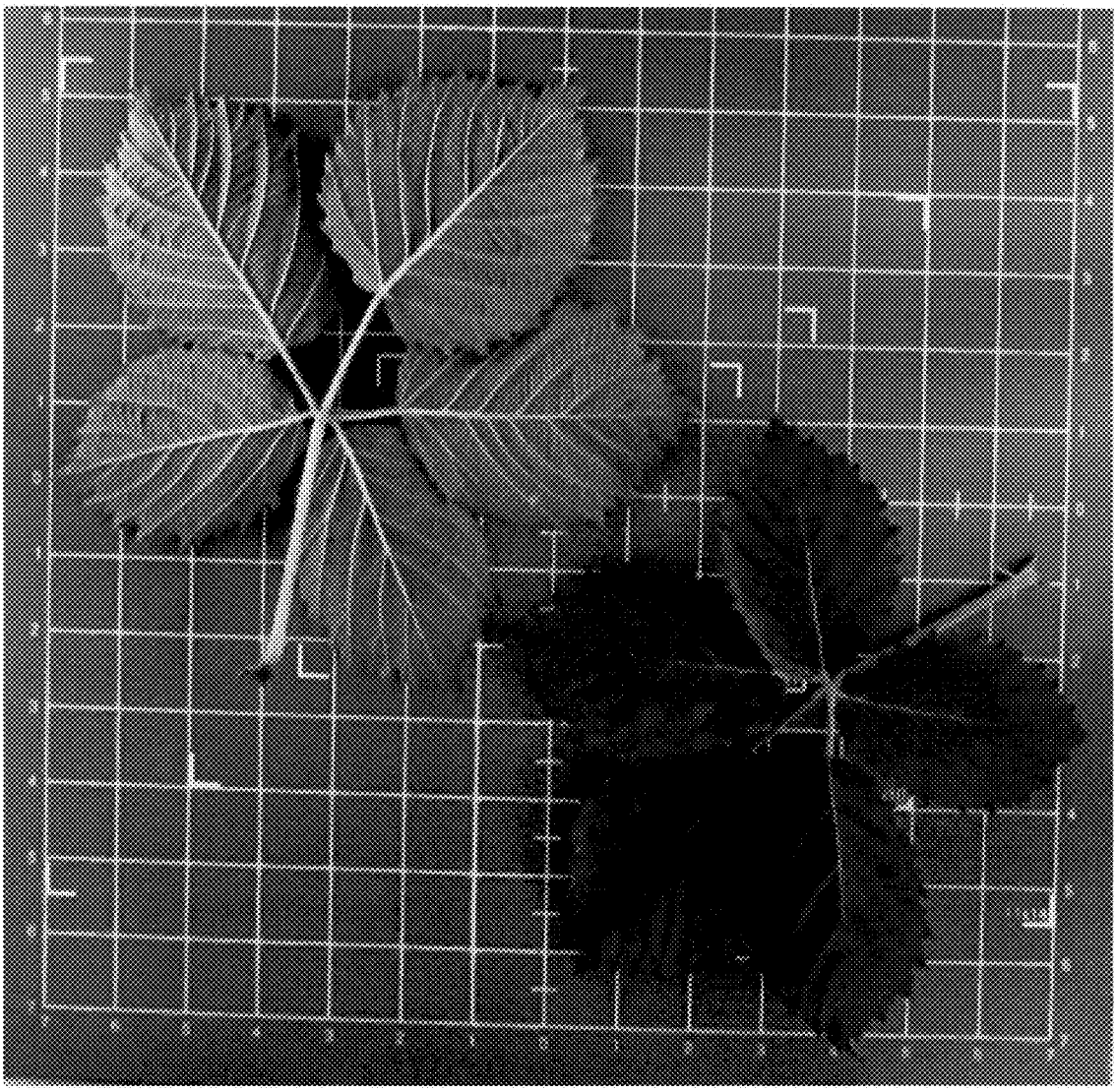
FIG. 4 is a photograph showing the abaxial (left) and adaxial (right) surfaces of primocane leaves collected from a three-year-old plant, near Clarksville, Ark. of 'APF-409T'.

Plants and fruit of this new cultivar differ phenotypically from its parents. The new blackberry plant produces fruit on primocanes, whereas the female parent, 'A-2504T', only produces fruit on floricanes. The new blackberry plant blooms and ripens earlier on primocanes than the male parent, 'APF-295T'. Although blackberries (*Rubus* L. subgenus *Rubus* Watson) are highly heterogeneous and outcrossing, and most cultivars are interspecific hybrids, the new cultivar and its progenitor lines phenotypically exhibit characteristics predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes are best managed if trained to a hedgerow and a trellis with supporting wires used to prevent canes from falling over due to wind or heavy fruit loads. The plants are thornless. Plants and fruit are moderately resistant to anthracnose [*Elsinoe veneta* (Burkh.) Jenkins], and plants have shown no evidence of susceptibility to orange rust [*Gymnoconia nitens* (Schwein.) F. Kern and H. W. Thurston.]. No screening has been done for resistance to double blossom/rosette [*Cercosporella rubi* (Wint.) Plakidas].

Plants and fruit of this new cultivar differ phenotypically from similar varieties. The average floricane bloom of the new cultivar peaks on 28 April, compared to 2 May for 'APF-45' (U.S. Plant Pat. No. 22,449) and 6 May for 'APF-190T' (U.S. Plant Pat. No. 28,598). The first harvest of floricane fruit of the new cultivar begins on 1 June, compared to average first harvest on 'APF-190T' (6 June) and 'APF-45' (9 June). Primocane first ripe fruit date is 10 July on tipped primocanes, whereas 'APF-190T' is first ripe on 30 July and 'APF-45' is first ripe on 8 August.

Fruit yields of the new cultivar on floricanes average 3.4 kg/plant (7.7 lb/plant) similar to 3.0-4.0 kg/plant (6-9 lb/plant) for 'APF-45' and greater than 1.1 kg/plant (2.4 lb/plant) for 'APF-190T' in West-Central Arkansas. Fruit yields of the new cultivar on primocanes in West-Central Arkansas average 1.4 kg/plant (3.1 lb/plant) compared to 1.8 kg (4.0 lb/plant) for 'APF-45' and 0.6 kg/plant (1.3 lb/plant) for 'APF-190T'. Primocane fruit harvest can be dependent on environmental conditions, most importantly temperatures being below 32° C. (90° F.) to allow fruiting.

The fresh fruit rates good in flavor, comparable to comparison cultivars. The soluble solids concentration averages 11.7% on shiny black fruit harvested from floricanes and 11.9% from primocanes. Soluble solid content is higher than that of 'APF-45', which averages 9.7% and 9.9% for floricane and primocane fruit, respectively.

Primocane fruit and flowers are borne on the cane terminus or on lateral branches if primocanes are tipped, and fruiting continues down the primocane during the season. Canes usually attain a length of approximately 1.8 m (4 ft) prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown in a fine sandy loam soil with trickle irrigation near Clarksville, Ark. The plants were fertilized near budbreak (February to March) with complete or nitrogen fertilizer, and had an additional nitrogen fertilizer application in early July. Primocanes were tipped at approximately 1.14 m (45 inches), and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Medium. Plants are grown in a hedgerow and primocanes tipped at approx. 114 cm; plants in this system range in size from approx. 135-140 cm tall and 91-102 cm wide.

*Growth habit*.—Moderate vigor, canes erect; suckers primarily from the crown of the plant.

*Growth rate*.—First emergence of primocanes is 26 April and primocanes reach tipping height (114 cm) approximately 10 May.

Productivity:

*Floricane*.—3.4 kg/plant (7.7 lb/plant).

*Primocane*.—1.4 kg/plant (3.1 lb/plant).

*Cold hardiness*.—Hardy to −17° C. (1° F.) and possibly lower. Significant damage to floricanes was noted at −26° C. (−15° F.).

*Canes*.—Thornless, erect.

*Disease resistance*.—Moderate resistance to anthracnose, and no evidence of orange rust disease. No screening has been done for resistance to double blossom/rosette.

Floricane (dormant or winter cane):

*Cane diameter*.—Base: 1.4 cm; midpoint: 0.9 cm; terminus: 0.61 cm.

*Internode length*.—Base: 6.2 cm; midpoint: 5.7 cm; terminus: 3.1 cm.

*Floricane color*.—Base: greyed-purple group (183A) on sun exposed side, yellow-green group (145A) on shaded side; midpoint: greyed-purple group (183C) on sun exposed side, yellow-green group (145A) on shaded side; terminus: greyed-purple group (183C) on sun exposed side, yellow-green group (145A) on shaded side.

*Thorn density/30 cm*.—Not applicable; this plant is thornless.

*Thorn size*.—Not applicable; this plant is thornless.

*Thorn color*.—Not applicable; this plant is thornless.

*Lateral branching after tipping* (*measured at the end of growing season*).—Average number of lateral branches: 5; distribution: over whole length of the plant; anthocyanin present: yes; color: red group (44A).

*Shape of dormant cane cross-section*.—Round near base and midpoint, gradually getting more angular near the terminus.

Primocane (current-season cane):

*Number of new canes per season*.—3.

*Cane diameter*.—Base: 1.7 cm; midpoint: 1.2 cm; terminus: 1.0 cm.

*Internode length*.—Base: 6.7 cm; midpoint: 6.5 cm; terminus: 2.8 cm.

*Primocane color*.—Base: yellow-green group (144B); midpoint: yellow-green group (144B); terminus: yellow-green group (144B). No anthocyanin coloration present on primocanes.

*Thorn density/30 cm*.—None, this plant is thornless.

*Thorn size*.—Not applicable; this plant is thornless.

*Thorn color*.—Not applicable; this plant is thornless.

*Lateral branching after tipping* (*measured at the end of growing season*).—Average number of lateral branches: 5; distribution: over whole length of the plant.

*Relative number of glandular hairs on young shoot*.—Absent or few.

Foliage (floricane):

*Leaves*.—Shape: compound palmate leaf; size: width: 11.3 cm; length: 9.3 cm; budbreak: 15 February.

*Glossiness*.—Abaxial: absent, dull; adaxial: moderate.

*Leaflet*.—Width: 4.0 cm; length: 6.4 cm; overall shape: lanceolate; shape at base: cordate; shape at apex: acute; margin shape: biserrate; serration teeth length: 2.0 mm; width: at base: 2.0 mm; shape in cross section: u-shaped; degree of undulation on terminal leaflet: absent or very weak; degree of blistering on terminal leaflet: weak.

*Pubescence*.—Abaxial: heavy; adaxial: medium.

*Number of leaflets per compound leaf*.—3.

*Leaf color*.—Base: abaxial: yellow-green group (147B), adaxial: green group (139A); midpoint: abaxial: yellow-green group (147B), adaxial: green group (139A); terminus: abaxial: yellow-green group (147B), adaxial: green group (139A).

*Petioles*.—Length: 1.1 cm; diameter: 1.2 mm; color: yellow-green group (147C); texture: moderate pubescence present.

*Petiolules*.—Length: 6.0 cm; diameter: 1.9 mm; color: yellow-green group (144A); texture: moderate pubescence present.

*Stipule*.—Number present: 2.

*Stipule size*.—Length: 1.4 cm; width: 1.5 mm.

*Stipule shape*.—Overall: linear; apex: acute; margin: entire (smooth); base: truncate.

*Stipule texture*.—Abaxial: heavy pubescence; adaxial: moderate pubescence.

*Stipule color*.—Abaxial: yellow-green group (146B); adaxial: green group (137A).

*Venation pattern*.—Pinnate.

*Vein color* (*mature leaves*).—Abaxial: yellow-green group (147C); adaxial: yellow-green group (147C).

*Vein color* (*young leaves*).—Abaxial: yellow-green group (145C); adaxial: yellow-green group (145B).

Foliage (primocane):

*Leaves*.—Shape: compound palmate leaf; size: width: 18.4 cm; length: 18.8 cm.

*Glossiness*.—Abaxial: absent, dull; adaxial: moderate sheen.

*Leaflet*.—Width: 8.2 cm; length: 9.6 cm; overall shape: lanceolate; shape at base: cordate; shape at apex: acute; margin shape: biserrate; serration teeth length: 1.6 mm; width: at base: 2.1 mm; leaflet shape in cross section: u-shaped; degree of undulation on terminal leaflet: absent to weak; degree of blistering on terminal leaflet: moderate.

*Pubescence*.—Abaxial: heavy; adaxial: absent to weak.

*Number of leaflets per compound leaf*.—5.

*Leaf color*.—Base: abaxial yellow-green group (146B), adaxial: yellow-green group (137A); midpoint: abaxial: yellow-green group (146B), adaxial: green group (137A); terminus: abaxial: yellow-green group (146B), abaxial: green group (137A).

*Petioles*.—Length: 8.7 cm; diameter: 4.8 mm color: yellow-green group (146B); texture: weak to moderate pubescence present.

*Petiolules*.—Length: 4.2 cm; diameter: 2.2 mm; color: yellow-green group (146C); texture: moderate pubescence present.

*Stipule*.—Number present: 2.

*Stipule size*.—Length: 1.4 mm; width: 2.2 mm.

*Stipule shape*.—Overall: subulate; apex: acuminate; margin: entire (smooth); base: rounded.

*Stipule texture*.—Abaxial: heavy pubescence present; adaxial: weak to moderate pubescence present.

*Stipule color*.—Abaxial: yellow-green group (146B); adaxial: yellow-green group (146A).

*Venation pattern*.—Pinnate.

*Vein color* (*mature leaves*).—Abaxial: yellow-green group (146C); adaxial: yellow-green group (146D).

*Vein color* (*young leaves*).—Abaxial: yellow-green group (146C); adaxial: yellow-green group (146D).

Flowers (floricane):

*Date of first bloom*.—28 April.

*Reproductive organs*.—

*Stamens*.—Numerous.

*Pistils*.—Numerous.

*Pollen*.—Normal, fertile, and abundant.

*Flower*.—Size: diameter: 3.7 cm; depth: 1.7 cm; shape: overall: rotate; symmetry: actinomorphic.

*Petal size*.—Length 1.9 cm; width 1.3 cm.

*Petal shape*.—Overall: obovate; apex: obtuse; margin: smooth (entire); base: cuneate.

*Petal texture*.—Abaxial: smooth, no pubescence; adaxial: smooth, no pubescence.

*Petal color*.—Abaxial: white group (155D); adaxial: white group (155D).

*Average number flowers per cluster*.—5.

*Average number of petals per flower.*—5.

*Sepals.*—Length 0.78 cm; width: 0.52 cm; shape: overall: cordate; apex: aristate; margin: entire (smooth); base: truncate; texture: abaxial: heavy pubescence; adaxial: moderate to heavy pubescence; color: abaxial: yellow group (11B); adaxial: yellow-green group (146D); number per flower: 5.

*Pedicel.*—Length: 3.5 cm; diameter: 1.5 mm; color: yellow-green group (144A); texture: heavy pubescence.

*Peduncle.*—Size: length: 10.4 cm; width: 3.2 mm; color: yellow-green group (144A).

*Cyme type.*—Simple cyme; length: 8.9 cm.

Flowers (primocane):

*Date of bloom.*—First bloom averages 31 May and can extend until frost depending on environment and cultural management.

*Reproductive organs.*—

*Stamens.*—Numerous.

*Pistils.*—Numerous.

*Pollen.*—Fertile and abundant unless temperatures exceed 32° C. (90° F.) at which temperature can damage flowers and anthers and pollen production can be reduced.

*Flower.*—Size: diameter: 2.9 cm; depth: 1.2 cm; shape: overall: rotate; symmetry: actinomorphic.

*Petal size.*—Length: 1.3 cm; width: 0.9 cm.

*Petal shape.*—Overall: obovate; apex: obtuse; margin: entire (smooth); base: cuneate.

*Petal texture.*—Abaxial: smooth, no pubescence; adaxial: smooth, no pubescence.

*Petal color.*—Abaxial: white group (155B); adaxial: white group (155A).

*Average number flowers per cluster.*—5.

*Average number of petals per flower.*—5.

*Sepals.*—Length 0.81 cm; width: 5.6 cm; shape: overall: lanceolate; apex: aristate; margin: entire (smooth); base: truncate; texture: abaxial: smooth, no pubescence; adaxial: smooth, no pubescence; color: abaxial: yellow-green group (147D); adaxial: yellow-green group (144A); number per flower: 5.

*Pedicel.*—Length: 2.8 cm; diameter: 1.6 mm; color: yellow-green group (144A); texture: heavy pubescence.

*Peduncle.*—Size: length: 3.8 cm; width: 3.5 mm; color: green group (143C).

*Cyme type.*—Elongated simple cyme; length: 11.3 cm.

Fruit (floricane):

*Maturity.*—Average first ripe date 1 June.

*Size.*—Medium, average 7.6 g.

*Diameter of fruit at primary position on inflorescence.*—Equator: 1.9 cm; base pole: 1.9 cm; terminus pole: 1.6 cm.

*Diameter of fruit at secondary positions on inflorescence.*—Equator: 1.8 cm; base pole: 1.6 cm; terminus pole: 1.4 cm.

*Length (primary fruit).*—2.7 cm.

*Length (secondary fruit).*—2.4 cm.

*Length (tertiary fruit).*—2.2 cm.

*Shape.*—Medium ovate.

*Color.*—Black group (202A).

*Drupelet size.*—Length: 5.0 mm.

*Drupelets per berry.*—66.

*Seed size.*—Length: 3.1 mm; width: 2.4 mm.

*Seed weight.*—Wet: 6.3 mg; dry: 3.6 mg.

*Seed color.*—Wet: orange-red group (34B); dry: yellow-orange group (22B).

*Soluble solids.*—11.7%.

*pH.*—3.66.

*Titratable acidity.*—1.0% citric acid.

*Processed quality.*—Not evaluated for processing.

*Uses.*—For home garden, local fresh-market, or commercial shipping.

Fruit (primocane):

*Maturity.*—Average first ripe date 10 July on tipped primocanes and can fruit until frost depending on environment and cultural management.

*Size.*—Medium, 6.5 g/berry.

*Diameter of fruit at primary position on inflorescence.*—Equator: 2.0 cm; base pole: 1.7 cm; terminus pole: 1.2 cm.

*Diameter of fruit at secondary positions on inflorescence.*—Equator: 2.1 cm; base pole: 1.8 cm; terminus pole: 1.3 cm.

*Length (primary fruit).*—2.5 cm.

*Length (secondary fruit).*—2.3 cm.

*Length (tertiary fruit).*—2.2 cm.

*Shape.*—Medium ovate.

*Color.*—Black group (202A).

*Drupelet size.*—Length: 5.8 mm.

*Drupelets per berry.*—65.

*Seed size.*—Length: 3.6 mm; width: 2.0 mm.

*Seed weight.*—Wet: 1.1 mg; dry: 0.5 mg.

*Seed color.*—Wet: orange-red group (35D); dry: red group (36C).

*Soluble solids.*—11.9%.

*pH.*—1.0.

*Titratable acidity.*—3.47% citric acid.

*Processed quality.*—Not evaluated for processing.

*Uses.*—For home garden, local fresh-market, or commercial shipping.

The cultivar: The most distinctive features of the new cultivar of blackberry plant are excellent plant health, thornless canes, strong primocane-fruiting tendency, and early season of fruit ripening on both floricanes and primocanes.

I claim:

1. A new and distinct cultivar of blackberry plant named 'APF-409T', substantially as illustrated and described.

* * * * *